(12) United States Patent
Ellern et al.

(10) Patent No.: US 9,107,420 B2
(45) Date of Patent: Aug. 18, 2015

(54) ANIMAL SHAMPOO

(71) Applicants: Eliana Ellern, Miami, FL (US); Joshua A Ellern, Miami, FL (US)

(72) Inventors: Eliana Ellern, Miami, FL (US); Joshua A Ellern, Miami, FL (US)

( * ) Notice: Subject to any disclaimer, the term of this patent is extended or adjusted under 35 U.S.C. 154(b) by 0 days.

(21) Appl. No.: 14/099,156

(22) Filed: Jan. 13, 2014

(65) Prior Publication Data

US 2015/0196035 A1 Jul. 16, 2015

(51) Int. Cl.
*A61K 8/97* (2006.01)
*A01N 65/08* (2009.01)
*A61K 8/92* (2006.01)

(52) U.S. Cl.
CPC ............... *A01N 65/08* (2013.01); *A61K 8/922* (2013.01); *A61K 8/97* (2013.01)

(58) Field of Classification Search
None
See application file for complete search history.

(56) References Cited

U.S. PATENT DOCUMENTS

| | | | |
|---|---|---|---|
| 4,933,371 A | 6/1990 | Hink | |
| 5,405,609 A * | 4/1995 | Sanchez | ........................ 424/744 |
| 6,685,954 B2 | 2/2004 | Jeannin | |
| 7,393,528 B2 | 7/2008 | Tvedten | |
| 7,902,140 B1 | 3/2011 | Hansen | |
| 8,293,286 B2 | 10/2012 | Nouvel | |
| 8,361,515 B2 | 1/2013 | Wei | |
| 2004/0241194 A1 | 12/2004 | Picaud | |
| 2007/0190094 A1 | 8/2007 | Bessette | |
| 2008/0107640 A1 | 5/2008 | Tvedten | |
| 2008/0193387 A1 | 8/2008 | DeWolff | |
| 2008/0249161 A1 | 10/2008 | Fabries | |
| 2009/0030087 A1 | 1/2009 | Chiasson | |
| 2009/0099135 A1 | 4/2009 | Enan | |
| 2009/0186096 A1 | 7/2009 | Kritzman | |
| 2010/0272818 A1 | 10/2010 | Franklin | |
| 2010/0303940 A1 | 12/2010 | Enan | |
| 2010/0316738 A1 | 12/2010 | Jimenez | |
| 2011/0195137 A1 | 8/2011 | Fabries | |
| 2012/0219518 A1 * | 8/2012 | Serra | .............................. 424/74 |
| 2012/0251641 A1 | 10/2012 | Enan | |

FOREIGN PATENT DOCUMENTS

JP 2001122763 A * 5/2001

* cited by examiner

Primary Examiner — Susan Hoffman
(74) Attorney, Agent, or Firm — Christopher J. Vandam, PA; Chris Vandam

(57) ABSTRACT

An animal shampoo that can be used for washing animals or for topical treatment to areas that are occupied by animals including soap, water, vinegar, epazote and glycerin (or olive oil) is taught. Other optional ingredients and variations of the primary ingredients are also disclosed.

3 Claims, 1 Drawing Sheet

Figure 1: Table 1

| Ingredient | Ideal percentage by volume |
|---|---|
| Castile soap | 50 |
| White (or apple cider) vinegar | 25 |
| Vegetable glycerine (or olive oil) | 6 |
| Water | 15 |
| Epazote powder | 3 |
| Essential oils or neem oil | 1 |

Figure 2: Table 2

| Ingredient | Percentage range by volume |
|---|---|
| Castile soap | 40-60 |
| White (or apple cider) vinegar | 20-30 |
| Vegetable glycerine (or olive oil) | 4-8 |
| Water | 12-18 |
| Epazote powder | 2-10 |
| Optional: Essential oils or neem oil | 0-2 |

ANIMAL SHAMPOO

BACKGROUND OF THE INVENTION

1. Field of the Invention

The present invention relates to animal skin & or fur treatments, and more particularly, to a non invasive natural shampoo for humans and animals to prevent or holistically treat infestation of ticks, fleas and other insect pests.

2. Description of the Related Art

Several formulas for pet shampoos have been designed in the past. None of them, however, include Epazote, scientifically known as *Dysphania ambrosioides* or *Chenopodium ambrosioides* ("the Plant") in its natural form or any derivatives such as Ascaridole or other terpenes extracted from the Plant.

In the early 1900s the Plants' oil was used as a major anthelmintic (medicine for controlling internal parasites) to control hookworms in humans, cats, dogs, horses and pigs. It was known then as Baltimore oil. This use was discontinued due to its potential toxicity, caused mainly by Ascaridole, which makes up for anywhere between 40% and 70% of the plant.

United States Patent US 20100316738 A1 is an invention addressed to solve Ascaridole's toxicity (& obtaining as a result EPA approval) by extracting synthetically from the "plant" all the pesticide compositions comprising terpenes, except Ascaridole and use these compositions exclusively to kill, inhibit, prevent and or repel exclusively plant pests from contacting and or damaging plants.

Our invention unlike Patent US 20100316738 A1 is addressed to humans and animals and using homeopathic way by drying and powdering the Plant leaves instead of extracting its oil.

Other patents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide an external soap or shampoo based treatment applied to the fur of animals to prevent and treat tick and flea infestations.

It is another object of this invention to provide an organic formula for flea and tick treatments for animals that is derived without the use of harsh chemicals.

It is still another object of the present invention to provide a flea and tick remedy that is safe for pets and their owners It is yet another object of this invention to provide such a formula that is inexpensive to manufacture and maintain while retaining its effectiveness.

Further objects of the invention will be brought out in the following parts of the specification, wherein detailed description is provided for the purpose of fully disclosing the invention without placing specific limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 1 is a table showing an example of ingredients of a shampoo by percentage volume.

FIG. 2 is a table showing an example of ingredients of a shampoo by effective volume range.

DETAILED DESCRIPTION OF THE PREFERRED EMBODIMENT

Referring now to the drawings, where the present invention is generally described in the tables, it can be observed that it basically includes Castile soap, white vinegar (or apple cider vinegar), vegetable glycerin (or olive oil), water, epazote powder and neem oil (or essential oils).

Table 1 in FIG. 1 is an example of an effective formula organized by an ideal percentage by volume of each ingredient. It can be observed that is about 50 percent Castile soap, 25 percent white vinegar or apple cider vinegar, 6 percent vegetable glycerine or olive oil, 15 percent water, 3 percent epazone powder and 1 percent neem oil or other essential oils. This is but an example of a formula found to be effective and is intended to include variations.

The variations of the formula are found in table 2 in FIG. 2. It can be seen that the range by volume of ingredients is between 40 and 60 percent Castile soap, between 20 and 30 percent white vinegar (or apple cider vinegar), 4 to 8 percent vegetable glycerin (or olive oil), between 12 and 18 percent water, between 2 and 6 percent epazote powder and optionally up to 2 percent neem oil (or other essential oil).

In another variation of the formulation ascaridole can be substituted for the epazote powder in roughly the same volumetric proportions to the other ingredients as epazote is described.

Ascaridole is a natural organic compound classified as a bicyclic monoterpene that has an unusual bridging peroxide functional group. It is a colorless liquid with a pungent smell and taste that is soluble in most organic solvents. Ascaridole determines the specific flavor of the Chilean tree boldo and is a major constituent of the oil of Mexican Tea (wormseed). It is a component of natural medicine, tonic drinks and food flavoring in some Latin American cuisine. As part of the oil, ascaridole is used as an anthelmintic drug that expels parasitic worms from plants, domestic animals and the human body.

Ascaridole is mainly used as an anthelmintic drug that expels parasitic worms (helminths) from body and plants. This property gave the name to this chemical, after *Ascaris*—a genus of the large intestinal roundworms. In the early 1900s, it was a major remedy against intestinal parasites in humans, cats, dogs, goats, sheep, chickens, horses and pigs, and it is still used in livestock, particularly in the Central American countries. The dosage was specified by the ascaridole content in the oil, which was traditionally determined with an assay.

The wormseed plant itself (also known as Mexican Tea) is traditionally used in Mexican cuisine for flavoring dishes and preventing flatulence from bean-containing food. It is also sometimes part of tonic drinks and infusions to expel intestinal parasites and treat asthma, arthritis, dysentery, stomach ache, malaria and nervous diseases in folk medicine practiced in North and South Americas, China, Turkey and other countries around the world.

In an important version of the formulation the essential oils are organically derived. Currently, according to the US Department of Agriculture (USDA), organic plants are produced by farmers who emphasize the use of renewable resources and the conservation of soil and water to enhance environmental quality for future generations. Organic plants are produced without using most conventional pesticides, fertilizers made with synthetic ingredients (including sewage sludge), bioengineering, or ionizing radiation. Generally, before a product can be labeled "organic," a government-approved certifier inspects the farm where the food is grown to make sure the farmer is following all the rules necessary to meet USDA organic standards.

An effective variation of the formula can be made from:

½ cup of liquid Castile soap;
¼ cup white vinegar (or apple cider vinegar);
1 Tablespoon vegetable glycerin (or olive oil);
2 Tablespoons of water;
½ Tablespoon to 1 Tablespoon powder of epazote;
Optionally add: 3 or 4 drops of essential oils
Optionally add: 2 Drops of Neem Oil
Procedure to make and use:
Use a funnel to pour one ingredient at a time to small bottle with a cap or lid.

Shake well after the addition of each ingredient. The Castile soap will help to hold the ingredients together. Shake the shampoo before each use to ensure it is properly mixed.

Obviously, this formula could be scaled up or down as long as the proportions are maintained.

Generally, the epazote powder can vary and be effective anywhere between about two percent and ten percent of the formula by volume.

The most popular essential oils that are used as part of the formula include, by way of example only, sweet orange, *mentha arvensis*, peppermint, cedarwood, lemon, *eucalyptus globulus, litsea cubeba*, clove (leaf) or spearmint. Other essences or essential compounds can be used to enhance the smell and other characteristics of the shampoo.

Castile soap is generally an olive oil or laurel oil based soap. It can signify a soap made in the traditions and style of soap made in the Castile region of Spain. Presently, Castile soap is made in many regions around the world and not necessarily a product of Spain. Although Castile soap is a proven effective ingredient in the described formula, other soaps, detergents and emulsifiers can also be effective.

The shampoo can be used in similar fashion to other shampoos wherein the animal is wetted with water and a diluted solution of the shampoo is worked into the coat or fur of the animal and then rinsed out with clean water.

The soap can also be used at full strength or diluted and spread around the quarters of the animal, in bedding material and around areas where the animals congregate or transit. For example, around paddocks, stables, pens, stalls, cages, corrals, hutches, coops and similar types of animal housing.

The soap can be used on most types of mammals including domestics and livestock. The soap can be used as a preventative measure or remedial when an insect problem is already apparent either directly on the animal or in close proximity to the animal.

A preferred course of treatment is to wash the affected animals at least twice a week or other periods as recommended by a veterinarian for the particular insect and host animal under treatment regimen. Prior to use of the soap and periodically during treatment is also recommended to use best practices to reduce other sources of insect infestation including feed storage, bedding materials and other recognized contributing factors to an infestation.

A shampoo can be fairly described as including the following ingredients by volume: 40-60% Castile soap, 20-30% vinegar, 4-8% vegetable glycerin or olive oil, 12-18% water, 2-6% epazote powder and 0-2% essential oil. Optionally, the vinegar can any ratio or combination of white vinegar and/or apple cider vinegar. Optionally, the essential oil is any individual or combination selected from the group of neem oil, sweet orange, *mentha arvensis*, peppermint, cedarwood, lemon, *eucalyptus globulus, litsea cubeba*, clove (leaf) or spearmint. A shampoo can be fairly described as a shampoo including between 2 and 6 percent epazote by volume.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. An animal shampoo comprised of a mixture of the following ingredients by volume:
   40-60% Castile soap;
   20-30% vinegar;
   4-8% vegetable glycerin or olive oil;
   12-18% water;
   2-6% epazote powder; and
   0-2% essential oil.

2. The animal shampoo as in claim 1 further characterized in that the vinegar is white vinegar; apple cider vinegar, or a combination thereof.

3. The animal shampoo as in claim 1 further characterized in that the essential oil is selected from the group consisting of neem oil, sweet orange, *mentha arvensis*, peppermint, cedarwood, lemon, *eucalyptus globulus, litsea cubeba*, clove leaf, or spearmint, or any combination thereof.

* * * * *